United States Patent
Giampapa

(10) Patent No.: US 8,974,839 B2
(45) Date of Patent: *Mar. 10, 2015

(54) DIETARY SUPPLEMENT SYSTEM FOR MULTIFUNCTIONAL ANTI-AGING MANAGEMENT AND METHOD OF USE

(71) Applicant: Vincent C. Giampapa, Montclair, NJ (US)

(72) Inventor: Vincent C. Giampapa, Montclair, NJ (US)

(73) Assignee: Cellhealth Technologies Ltd., Montclair, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/262,479

(22) Filed: Apr. 25, 2014

(65) Prior Publication Data

US 2014/0308248 A1    Oct. 16, 2014

Related U.S. Application Data

(63) Continuation of application No. 13/573,386, filed on Sep. 13, 2012, now Pat. No. 8,747,915.

(60) Provisional application No. 61/534,673, filed on Sep. 14, 2011.

(51) Int. Cl.

| | |
|---|---|
| *A61K 36/00* | (2006.01) |
| *A23L 1/48* | (2006.01) |
| *A61K 36/03* | (2006.01) |
| *A61K 36/16* | (2006.01) |
| *A61K 36/48* | (2006.01) |
| *A61K 36/53* | (2006.01) |
| *A61K 36/81* | (2006.01) |
| *A61K 36/84* | (2006.01) |
| *A61K 36/87* | (2006.01) |
| *A61K 36/8998* | (2006.01) |
| *A61K 36/9066* | (2006.01) |
| *A61K 38/54* | (2006.01) |

(52) U.S. Cl.
CPC . *A61K 38/54* (2013.01); *A23L 1/48* (2013.01); *A61K 36/00* (2013.01); *A61K 36/03* (2013.01); *A61K 36/16* (2013.01); *A61K 36/48* (2013.01); *A61K 36/53* (2013.01); *A61K 36/81* (2013.01); *A61K 36/84* (2013.01); *A61K 36/87* (2013.01); *A61K 36/8998* (2013.01); *A61K 36/9066* (2013.01); *A61K 2300/00* (2013.01)
USPC ............ 424/725; 426/531; 426/542; 426/615

(58) Field of Classification Search
USPC .......................... 424/725; 426/531, 542, 615
See application file for complete search history.

(56) References Cited

U.S. PATENT DOCUMENTS

| | | |
|---|---|---|
| 5,895,652 A | 4/1999 | Giampapa |
| 7,670,612 B2 | 3/2010 | Miller |
| 8,747,915 B1 | 6/2014 | Giampapa |

*Primary Examiner* — Rosanne Kosson
(74) *Attorney, Agent, or Firm* — Conley Rose, P.C.; Jerry C. Harris, Jr.

(57) ABSTRACT

A dietary supplement system includes a dietary supplement composition for oral administration by an individual in the morning, the composition, including (a) a telomere maintenance complex including: Purslane extract (aerial parts); Turmeric rhizome extract (95% curcuminoids); Quercetin dehydrate, Cayenne pepper fruit; Vanadium (as vanadyl sulfate); Fenugreek seed; *Astragalus* root extract, Omega fatty acid complex including linoleic acid; alpha-linolenic acid; oleic acid borage seed oil gamma-linolenic acid), evening primrose oil fish body oil (eicosapentaenoic acid; docosahexaenoic acid); (b) a calorie restriction mimetics and gene expression complex including Trans-resveratrol (from *Polygonum cuspidatum* root extract); Pterostilbene Fisetin 50% (*Buxus microphlla* Sieb (stem and leaf; Alpha lipoic acid, Coenzyme Q-10, Betaine HCl, Sulfur (from methylsulfonylmethane); L-Carnitine tartrate; L-Carnitine HCl, and (c) a free radical scavenger complex, including Green tea leaf extract catechin and polyphenols); Anthocyanins (from bilberry fruit and grape skin extracts).

5 Claims, No Drawings

DIETARY SUPPLEMENT SYSTEM FOR MULTIFUNCTIONAL ANTI-AGING MANAGEMENT AND METHOD OF USE

CROSS-REFERENCE TO RELATED APPLICATION

This application is a continuation of U.S. patent application Ser. No. 13/573,386 filed Sep. 13, 2012 and titled "Dietary Supplement System for Multifunctional Anti-Aging Management and Method of Use," which claims priority to U.S. Provisional Patent Application No. 61/534,673 filed Sep. 14, 2011. The content of each of these applications is hereby incorporated by reference herein in its entirety for all purposes.

BACKGROUND

The aging process is believed to relate to the failure of cell components such as the cell nucleus to continue to replicate otherwise healthy cells. This is believed to occur as a result of damage which occurs to essential cell components resultant of decrease in levels of key chemical agents or substances involved in cellular regulation and production. These agents will typically diminish as a result of reduction in efficiency over time of glands and organs in the human body. Reductions in such key chemical agents are believed to cause damage to the RNA and DNA in each cell nucleus which thereby reduces the ability of the cell to reproduce itself which ultimately brings on the aging process which yet further accelerates the decrease in body's production of the key agents. Therefore, the essential problem in anti-aging management is that of maintaining appropriate levels of key metabolic agents so that the genetic material within each cell will not become damaged or otherwise lose efficiency.

Therefore, it is desirable to have improved dietary supplement compositions that provide nutrients and substances to effectively support optimal cellular functions for the purpose of anti-aging management at both the cellular and organ levels.

SUMMARY

A dietary supplement system includes a first dietary supplement composition for oral administration by an individual in the morning, said first composition, comprising: (a) a telomere maintenance complex comprising: Purslane extract (aerial parts), 4-6 mg; Turmeric rhizome extract (95% curcuminoids), 20-30 mg; Quercetin dehydrate, 12-18 mg; Cayenne pepper fruit, 8-12 mg; Vanadium (as vanadyl sulfate), 20-30 mcg; Fenugreek seed, 20-30 mg; *Astragalus* root extract, 8-12 mg; Omega fatty acid complex, 160-240 mg, including linoleic acid (10.6%), alpha-linolenic acid (1.3%), oleic acid (1.6%), borage seed oil (10% gamma-linolenic acid), evening primrose oil (4.8% GLA), fish body oil (4.5% eicosapentaenoic acid, 3.0% docosahexaenoic acid); (b) a calorie restriction mimetics and gene expression complex comprising: Trans-resveratrol (from *Polygonum cuspidatum* root extract), 1.6-2.4 mg Pterostilbene (99%), 1.6-2.4 mg; Fisetin 50% (*Buxus microphlla* Sieb (stem and leaf)), 1.6-2.4 mg; Alpha lipoic acid, 8-12 mg; Coenzyme Q-10, 4-6 mg; Betaine HCl, 3.2-4.8 mg; Sulfur (from methylsulfonylmethane), 1-1.5 mg; L-Carnitine tartrate, 8-12 mg; L-Carnitine HCl, 4-6 mg; and (c) a free radical scavenger complex, comprising: Green tea leaf extract (40% catechin and polyphenols), 40-60 mg; Anthocyanins (from bilberry fruit and grape skin extracts), 4-6 mg.

DETAILED DESCRIPTION

In one embodiment, the present invention provides a dietary supplement system for supporting multifunctional anti-aging management. In one embodiment, the nutritional supplement system comprises two dietary supplement compositions, each for oral administration by an individual at a specific time of a day.

In one embodiment, each of the two dietary supplement compositions comprises multiple sub-functional groups of components, including telomere maintenance complex, calorie restriction mimetics and gene expression complex, free radical scavenger complex, DNA repair complex, stem cell maintenance complex, and cell regulation complex. Furthermore, the dietary supplement compositions also comprise multiple vitamins and minerals. One of the two supplement compositions is designated for oral administration in the morning, and hence is referred to as AM dietary supplement composition or AM composition hereinafter, and the other supplement composition is designated for oral administration in the evening, and hence is referred to as PM dietary supplement composition or PM composition hereinafter.

Unless defined otherwise, all technical and scientific terms used herein have the same meaning as commonly understood by one having ordinary skills in the art to which the invention belongs. It should also be understood that various individual components used herein may have more than one type of properties.

In the dietary supplement compositions, telomere maintenance complex comprises a group of components that individually and/or jointly support maintaining telomere of the chromosome. The telomere maintenance complex includes, but not limited to, purslane extract (aerial parts), turmeric rhizome extract containing curcuminoids, quercetin dehydrate, cayenne pepper fruit, vanadium, fenugreek seed, *astragalus* root extract, valerian root, omega fatty acid complex including linoleic acid, alpha-linolenic acid, and oleic acid, borage seed oil, evening primrose oil and fish body oil.

The calorie restriction mimetics and gene expression complex comprises a group of components that individually and/or jointly support calorie restriction mimetics and gene expression. The calorie restriction mimetics and gene expression complex includes, but not limited to, trans-resveratrol, such as from extract of *polygonum cuspidatum* root or grape skin, pterostilbene, fisetin, alpha lipoic acid, coenzyme Q-10, betaine HCl, sulfur, such as from methylsulfonylmethane, L-carnitine tartrate, L-carnitine HCl, acetyl-L-carnitine, and avocado extract.

The free radical scavenger complex comprises a group of components that individually and/or jointly function as antioxidant and reduce free radicals. The free radical scavenger complex includes, but not limited to, green tea leaf extract containing catechin and polyphenols, anthocyanins such as from bilberry fruit and grape skin extracts, *ginkgo biloba* leaf extract containing ginkgo flavonglycosides and sesquiterpene lactones, cruciferous vegetable concentrate (broccoli, kale, radish) containing glucosinolates, grape skin extract containing total phenolics, tomato lycopene extract containing lycopene, rosemary extract (aerial parts), pycnogenol (pine bark extract), lutein such as from marigold flower extract, and green barley grass (aerial parts).

The DNA repair complex comprises a group of components that individually and/or jointly support DNA repairing in both nuclei and mitochondria. The DNA repair complex includes, not limited to, water extract of *Uncaria tomentosa* containing carboxy alkyl esters, N-acetyl-cysteine, inositol hexaphosphate, and melatonin.

The stem cell maintenance complex comprises a group of components that individually and/or jointly support optimal maintenance of stem cells and gene expression. The stem cell maintenance complex includes, but not limited to, *chlorella* algae, *spirulina* algae, klamath blue-green algae, fuxoxanthin seaweed (whole plant), nori seaweed extract or brown seaweed extract.

The cell regulation complex comprises a group of components that individually and/or jointly support optimal cell regulation. The cell regulation complex includes, but not limited to, gotu kola leaf, phosphatidyl choline such as from soy lecithin, DMAE bitartrate, *cordyceps sinensis* mushroom extract containing cordyceptic acid, royal jelly 3× containing 10-HDA, l-glutamine, taurine, L-phenylalanine, tyrosine, inositol, L-arginine, L-ornithine, guarana seed extract, probiotic blend (*lactobacillus acidophilus, lactobacillus plantarum, bifidobacterium bifidum* and *lactobacillus casei*), amylase, neutral protease, cellulase, lactase, and lipase.

Multiple vitamins in the dietary supplement compositions include, but not limited to, vitamin A, vitamin C, vitamin D, vitamin E, vitamin K, thiamin, riboflavin, niacin, vitamin B6, folate, vitamin B12, biotin, and pantothenic acid.

The minerals in the dietary supplement compositions include, but not limited to iodine, calcium, zinc, selenium, copper, manganese, chromium, and molybdenum. Optionally, the minerals may further include transitional metal trace elements such as iridium, rhodium, ruthenium, and/or other transitional metal trace elements.

In addition to the active components described above, each composition may further include pharmaceutically acceptable medium. Pharmaceutically acceptable medium is known to those of ordinary skilled in the art. In one exemplary embodiment, the medium includes microcrystalline cellulose, croscarmellose sodium, stearic acid, calcium silicate, magnesium stearate, silica and film coat ingredients such as hypromellose, hydroxypropyl cellulose, and polyethylene glycol. The dietary supplement compositions can be made into various forms suitable for oral administration, for example powder, granules, capsules, tablets, or liquid.

In the AM and PM dietary supplement compositions, each sub-functional group may have some differences in the components described above, and the amount or concentration of individual components may be different, since the effects and needs between the two compositions provided at different times of a day may be different.

In one exemplary embodiment, the AM and PM dietary supplement compositions and the preferred amount of individual components are provided below in Table 1 and Table 2, respectively. It is noted that the amount of individual components is defined as the amount in one dosage or the amount of per serving, which can be contained in one or more capsules or tablets. For example, 20 to 30 mg of taurine in one dosage can be provided in one or two capsules. The size and number of capsules may depend on the manufacturability, which may further depend on the properties of the components and the pharmaceutically acceptable medium used therein.

TABLE 1

AM Dietary Supplement Composition

| Components | Amount Per Serving |
|---|---|
| Telomere Maintenance Complex | |
| Purslane extract (aerial parts) | 4-6 mg |
| Turmeric rhizome extract (95% curcuminoids) | 20-30 mg |
| Quercetin dihydrate | 12-18 mg |
| Cayenne pepper fruit | 8-12 mg |
| Vanadium (as vanadyl sulfate) | 20-30 mcg |
| Fenugreek seed | 20-30 mg |
| *Astragalus* root extract | 8-12 mg |
| Omega fatty acid complex including linoleic acid (10.6%), alpha-linolenic acid (1.3%), oleic acid (1.6%)), borage seed oil (10% gamma-linolenic acid), evening primrose oil (4.8% GLA), fish body oil (4.5% eicosapentaenoic acid, 3.0% docosahexaenoic acid) | 160-240 mg |
| Calorie Restriction Mimetics and Gene Expression Complex | |
| Trans-resveratrol (from *Polygonum cuspidatum* root extract) | 1.6-2.4 mg |
| Pterostilbene (99%) | 1.6-2.4 mg |
| Fisetin 50% (*Buxus microphlla* Sieb (stem and leaf)) | 1.6-2.4 mg |
| Alpha lipoic acid | 8-12 mg |
| Coenzyme Q-10 | 4-6 mg |
| Betaine HCl | 3.2-4.8 mg |
| Sulfur (from methylsulfonylmethane) | 1-1.5 mg |
| L-Carnitine tartrate | 8-12 mg |
| L-Carnitine HCl | 4-6 mg |
| Free Radical Scavenger Complex | |
| Green tea leaf extract (40% catechin and polyphenols) | 40-60 mg |
| Anthocyanins (from bilberry fruit and grape skin extracts) | 4-6 mg |
| *Ginkgo biloba* leaf extract (24% *ginkgo* flavonglycosides, 6% sesquiterpene lactones) | 40-60 mg |
| Green barley grass (aerial parts) | 20-30 mg |
| DNA Repair Complex | |
| water extract of *uncaria tomentosa* (containing carboxy alkyl esters) | 100-150 mg |
| N-acetyl-cysteine | 10-15 mg |
| Inositol hexaphosphate | 1.6-2.4 mg |

TABLE 1-continued

AM Dietary Supplement Composition

| Components | Amount Per Serving |
|---|---|
| Stem Cell Maintenance Complex | |
| *Chlorella* algae | 20-30 mg |
| *Spirulina* algae | 40-60 mg |
| Klamath blue-green algae | 60-90 mg |
| Fuxoxanthin seaweed (whole plant) | 20-30 mg |
| Nori seaweed extract | 1.6-2.4 mg |
| Cell Regulation Complex | |
| Gotu kola leaf | 8-12 mg |
| Phosphatidyl choline (from soy lecithin) | 20-30 mg |
| DMAE bitartrate | 20-30 mg |
| *Cordyceps sinensis* mushroom extract (1% cordyceptic acid) | 10-15 mg |
| Royal jelly 3X (5% 10-HDA) | 8-12 mg |
| L-Glutamine | 40-60 mg |
| Taurine | 20-30 mg |
| L-Phenylalanine | 20-30 mg |
| L-Tyrosine | 20-30 mg |
| Guarana seed extract (20% caffeine) | 32-48 mg |
| Amylase | 480-720 units |
| Neutral protease | 120-180 units |
| Cellulase | 4-6 units |
| Lactase | 80-120 units |
| Lipase | 2.6-3.9 units |
| Vitamins | |
| Vitamin A (as retinyl palmitate and 85% as beta-carotene) | 1,440-2,160 IU |
| Vitamin C (as ascorbyl palmitate and ascorbic acid) | 80-120 mg |
| Vitamin D (as cholecalciferol) | 32-48 IU |
| Vitamin E (as d-alpha tocopheryl succinate and from mixed natural tocopherols) | 40-60 IU |
| Vitamin K (as phytonadione) | 60-90 mcg |
| Thiamin (as thiamin HCl) | 4-6 mg |
| Riboflavin (as riboflavin and riboflavin-5-phosphate) | 3.2-4.8 mg |
| Niacin (as niacinamide and niacin) | 56-84 mg |
| Vitamin $B_6$ (as pyridoxine HCl and pyridoxal 5-phosphate) | 9.6-14.4 mg |
| Folate (as folic acid) | 40-60 mcg |
| Vitamin $B_{12}$ (as cyanocobalamin) | 64-96 mcg |
| Biotin | 40-60 mcg |
| Pantothenic acid (as D-calcium pantothenate) | 9.6-14.4 mg |
| Minerals | |
| Iodine (as potassium iodide and from kelp) | 24-36 mcg |
| Calcium (as calcium carbonate and citrate) | 240-360 mg |
| Zinc (as zinc glycinate) | 1.6-2.4 mg |
| Selenium (as selenomethionine) | 24-36 mcg |
| Copper (as copper lysinate) | 0.16-0.24 mg |
| Manganese (as manganese gluconate) | 0.16-0.24 mg |
| Chromium (as chromium polynicotinate) | 40-60 mcg |
| Molybdenum (as sodium molybdate) | 6.4-9.6 mg |
| Transitional metal trace elements including iridium, rhodium, ruthenium | 10-90 μg |

TABLE 2

PM Dietary Supplement Composition

| Component | Amount Per Serving |
|---|---|
| Telomere Maintenance Complex | |
| Purslane extract (aerial parts) | 4-6 mg |
| Turmeric rhizome extract (95% curcuminoids) | 20-30 mg |
| Quercetin dihydrate | 12-18 mg |
| Cayenne pepper fruit | 8-12 mg |
| Vanadium (as vanadyl sulfate) | 16-24 mcg |

TABLE 2-continued

PM Dietary Supplement Composition

| Component | Amount Per Serving |
|---|---|
| Fenugreek seed | 16-24 mg |
| Valerian root | 24-36 mg |
| Omega fatty acid complex including linoleic acid (10.6%), alpha-linolenic acid (1.3%), oleic acid (1.6%), borage seed oil (10% gamma-linolenic acid), evening primrose oil (4.8% GLA), fish body oil (4.5% eicosapentaenoic acid, 3.0% docosahexaenoic acid) | 160-240 mg |
| *Calorie Restriction Mimetics and Gene Expression Complex* | |
| Trans-resveratol (as *Polygonum cuspidatum* root extract or grape skin extract) | 1.6-2.4 mg |
| Pterostilbene | 1.6-2.4 mg |
| Fisetin 50% (*Buxus microphlla* Sieb (stem and leaf)) | 1.6-2.4 mg |
| Alpha-lipoic acid | 8-12 mg |
| Coenzyme $Q_{10}$ | 2.8-4.2 mg |
| Betaine (as betaine-HCl) | 2-3 mg |
| Sulfur (from methylsulfonylmethane) | 0.8-1.2 mg |
| L-Carnitine tartrate | 8-12 mg |
| Acetyl-L-carnitine | 4-6 mg |
| *Free Radical Scavenger Complex* | |
| Cruciferous vegetable concentrate (broccoli, kale, radish) (2% glucosinolates) | 32-48 mg |
| Grape skin extract (37% total phenolics) | 16-24 mg |
| Tomato lycopene extract (20% lycopene) | 1.6-2.4 mg |
| Rosemary 4:1 extract (aerial parts) | 2.6-3.9 mg |
| Pycnogenol (pine bark extract) | 1.32-1.98 mg |
| Lutein (from marigold flower extract) | 0.64-0.96 mg |
| Green barley grass | 8-12 mg |
| *DNA Repair Complex* | |
| Water extract of *uncaria tomentosa* (containing carboxy alkyl esters) | 100-150 mg |
| Inositol hexaphosphate | 1.6-2.4 mg |
| N-Acetyl cysteine | 6.4-9.6 mg |
| Melatonin | 0.4-0.6 mg |
| *Stem Cell Maintenance Complex* | |
| *Chlorella* algae | 20-30 mg |
| *Spirulina* algae | 12-18 mg |
| Klamath blue green algae | 36-54 mg |
| Fucoxanthin seaweed (whole plant) | 20-30 mg |
| Brown seaweed extract | 4-6 mg |
| *Cell Regulation Complex* | |
| Phosphatidylcholine (from soy lecithin) | 16-24 mg |
| *Cordyceps sinensis* mushroom extract (1% cordycepic acid) | 6.6-9.9 mg |
| Royal jelly 3x (5% 10-HDA) | 7.2-10.8 mg |
| Inositol | 40-60 mg |
| L-Glutamine | 200-300 mg |
| L-Arginine (as L-arginine HCl) | 128-192 mg |
| L-Ornithine (as L-ornithine HCl) | 96-144 mg |
| Taurine | 12.8-19.2 mg |
| L-Tyrosine | 16-24 mg |
| Probiotic blend including *Lactobacillus acidophilus*, *Lactobacillus plantarum*, *Bifidobacterium bifidum* and *Lactobacillus casei* | 40-60 million CFU |
| Amylase | 320-480 units |
| Neutral protease | 80-120 units |
| Lactase | 52-78 units |
| Lipase | 12.8-19.2 units |
| *Vitamins* | |
| Vitamin A (as retinyl palmitate and 85% from natural mixed carotenoids) | 1,120-1,680 IU |
| Vitamin C (as ascorbic acid and ascorbyl palmitate) | 160-240 mg |
| Vitamin D (as cholecalciferol) | 24-36 IU |
| Vitamin E (as d-alpha-tocopheryl succinate and from mixed natural tocopherols) | 32-48 IU |
| Vitamin K (as phytonadione) | 60-90 mcg |
| Thiamin (as thiamin HCl) | 2-3 mg |
| Riboflavin (as riboflavin and riboflavin-5-phosphate) | 4-6 mg |
| Niacin (as niacinamide and niacin) | 56-84 mg |
| Vitamin $B_6$ (as pyridoxine HCl and pyridoxal-5-phosphate) | 6-9 mg |
| Folate (as folic acid) | 64-96 mcg |
| Vitamin $B_{12}$ (as cyanocobalamin) | 96-144 mcg |

TABLE 2-continued

PM Dietary Supplement Composition

| Component | Amount Per Serving |
|---|---|
| Biotin | 32-48 mcg |
| Pantothenic acid (as D-calcium pantothenate) | 16-24 mg |
| Minerals | |
| Iodine (as potassium iodide and from kelp) | 9.6-14.4 mcg |
| Magnesium (as magnesium oxide and glycinate) | 106-159 mg |
| Zinc (as zinc glycinate) | 1.2-1.8 mg |
| Selenium (as selenomethionine) | 19.2-28.8 mcg |
| Copper (as copper lysinate) | 0.08-0.12 mg |
| Manganese (as manganese gluconate) | 0.08-0.12 mg |
| Chromium (as chromium polynicotinate) | 32-48 mcg |
| Molybdenum (as sodium molybdate) | 6.4-9.6 mcg |
| Transitional metal trace elements including iridium, rhodium, ruthenium | 10-90 µg |

Preferably, the AM dietary supplement composition is orally administered in the morning, and the PM dietary supplement composition is orally administered in the evening, for example at the bed time. Preferably, the dietary supplement compositions are administered daily as dietary or nutritional supplements. The compositions can be taken with or without food.

The unique combination of the above described telomere maintenance complex, calorie restriction mimetics and gene expression complex, free radical scavenger complex, DNA repair complex, stem cell maintenance complex, and cell regulation complex provides synergetic effects for optimal cellular function. The synergetic effects provide desired calorie restriction mimetics, reduce age related deteriorations in telomere maintenance, stem cell function, cell regulation and gene expression, reduce free radicals at cellular level, and enhance DNA repair in both nuclei and mitochondria. Moreover, the supplement compositions, through various components and their combination, further have anti-inflammation and anti-oxidation properties, and desired functions in regulating glycation and methylation. Therefore, the dietary supplement compositions provide a multifunctional and effective anti-aging management system.

The following example further describes and demonstrates embodiments within the scope of the present invention. The examples are given solely for the purpose of illustration and are not to be construed as limitations of the present invention, as many variations thereof are possible without departing from the spirit and scope of the invention.

EXAMPLE 1

An AM dietary supplement composition shown in Table 3 below was prepared, with the processes known in the art. The amount per serving described was provided in two capsules.

TABLE 3

Example AM Dietary Supplement Composition

| Component | Amount Per Serving |
|---|---|
| Telomere Maintenance Complex | |
| Purslane extract (aerial parts) | 5 mg |
| Turmeric rhizome extract (95% curcuminoids) | 25 mg |
| Quercetin dihydrate | 15 mg |
| Cayenne pepper fruit | 10 mg |
| Vanadium (as vanadyl sulfate) | 25 mcg |
| Fenugreek seed | 25 mg |
| *Astragalus* root extract | 10 mg |
| Omega fatty acid complex including linoleic acid (10.6%), alpha-linolenic acid (1.3%), oleic acid (1.6%), borage seed oil (10% gamma-linolenic acid), evening primrose oil (4.8% GLA), fish body oil (4.5% eicosapentaenoic acid, 3.0% docosahexaenoic acid) | 200 mg |
| Calorie Restriction Mimetics and Gene Expression Complex | |
| Trans-resveratrol (from *Polygonum cuspidatum* root extract) | 2 mg |
| Pterostilbene (99%) | 2 mg |
| Fisetin 50% (*Buxus microphlla* Sieb (stem and leaf)) | 2 mg |
| Alpha lipoic acid | 10 mg |
| Coenzyme Q-10 | 5 mg |
| Betaine HCl | 4 mg |
| Sulfur (from methylsulfonylmethane) | 1.25 mg |
| L-Carnitine tartrate | 10 mg |
| L-Carnitine HCL | 5 mg |
| Free Radical Scavenger Complex | |
| Green tea leaf extract (40% catechin and polyphenols) | 50 mg |
| Anthocyanins (from bilberry fruit and grape skin extracts) | 5 mg |
| *Ginkgo biloba* leaf extract (24% *ginkgo* flavonglycosides, 6% sesquiterpene lactones) | 50 mg |
| Green barley grass (aerial parts) | 25 mg |
| DNA Repair Complex | |
| Water extract of *uncaria tomentosa* (containing carboxy alkyl Vesters) | 125 mg |
| N-acetyl-cysteine | 12.5 mg |
| Inositol hexaphosphate | 2 mg |
| Stem Cell Maintenance Complex | |
| *Chlorella* algae | 25 mg |
| *Spirulina* algae | 50 mg |
| Klamath blue-green algae | 75 mg |
| Fuxoxanthin seaweed (whole plant) | 25 mg |
| Nori seaweed extract | 2 mg |
| Cell Regulation Complex | |
| Gotu kola leaf | 10 mg |
| Phosphatidyl choline (from soy lecithin) | 25 mg |
| DMAE bitartrate | 25 mg |
| *Cordyceps sinensis* mushroom extract (1% cordyceptic acid) | 12.5 mg |
| Royal jelly 3X (5% 10-HDA) | 10 mg |
| L-Glutamine | 50 mg |
| Taurine | 25 mg |

TABLE 3-continued

Example AM Dietary Supplement Composition

| Component | Amount Per Serving | |
|---|---|---|
| L-Phenylalanine | 25 | mg |
| L-Tyrosine | 25 | mg |
| Guarana seed extract (20% caffeine) | 40 | mg |
| Amylase | 600 | units |
| Neutral protease | 150 | units |
| Cellulase | 5 | units |
| Lactase | 100 | units |
| Lipase | 25 | units |
| Vitamins | | |
| Vitamin A (as retinyl palmitate and 85% as beta-carotene) | 1,800 | IU |
| Vitamin C (as ascorbyl palmitate and ascorbic acid) | 100 | mg |
| Vitamin D (as cholecalciferol) | 40 | IU |
| Vitamin E (as d-alpha tocopheryl succinate and from mixed natural tocopherols) | 50 | IU |
| Vitamin K (as phytonadione) | 75 | mcg |
| Thiamin (as thiamin HCl) | 5 | mg |
| Riboflavin (as riboflavin and riboflavin-5-phosphate) | 4 | mg |
| Niacin (as niacinamide and niacin) | 70 | mg |
| Vitamin $B_6$ (as pyridoxine HCl and pyridoxal 5-phosphate) | 12 | mg |
| Folate (as folic acid) | 50 | mcg |
| Vitamin $B_{12}$ (as cyanocobalamin) | 80 | mcg |
| Biotin | 50 | mcg |
| Pantothenic acid (as D-calcium pantothenate) | 12 | mg |
| Minerals | | |
| Iodine (as potassium iodide and from kelp) | 30 | mcg |
| Calcium (as calcium carbonate and citrate) | 300 | mg |
| Zinc (as zinc glycinate) | 2 | mg |
| Selenium (as selenomethionine) | 30 | mcg |
| Copper (as copper lysinate) | 0.2 | mg |
| Manganese (as manganese gluconate) | 0.2 | mg |
| Chromium (as chromium polynicotinate) | 50 | mcg |
| Molybdenum (as sodium molybdate) | 8 | mg |

Other ingredients: Microcrystalline cellulose, croscarmellose sodium, stearic acid, calcium silicate, magnesium stearate, silica and film coat ingredients (hypromellose, hydroxypropyl cellulose, and polyethylene glycol).

EXAMPLE 2

A PM dietary supplement composition shown in Table 4 below was prepared, with the processes known in the art. The amount per serving described was provided in two capsules.

TABLE 4

Example PM Dietary Supplement Composition

| Components | Amount Per Serving | |
|---|---|---|
| Telomere Maintenance Complex | | |
| Purslane extract (aerial parts) | 5 | mg |
| Turmeric rhizome extract (95% curcuminoids) | 25 | mg |
| Quercetin dihydrate | 15 | mg |
| Cayenne pepper fruit | 10 | mg |
| Vanadium (as vanadyl sulfate) | 20 | mcg |
| Fenugreek seed | 20 | mg |
| Valerian root | 30 | mg |
| Omega fatty acid complex including linoleic acid (10.6%), alpha-linolenic acid (1.3%), oleic acid (1.6%), borage seed oil (10% gamma-linolenic acid), evening primrose oil (4.8% GLA), fish body oil (4.5% eicosapentaenoic acid, 3.0% docosahexaenoic acid) | 200 | mg |
| Calorie Restriction Mimetics and Gene Expression Complex | | |
| Resveratol (as *Polygonum cuspidatum* root extract) | 2 | mg |
| Pterostilbene | 2 | mg |
| Fisetin 50% (*Buxus microphlla* Sieb (stem and leaf)) | 2 | mg |
| Alpha-lipoic acid | 10 | mg |
| Coenzyme $Q_{10}$ | 3.5 | mg |
| Betaine (as betaine-HCl) | 2.5 | mg |
| Sulfur (from methylsulfonylmethane) | 1 | mg |
| L-Carnitine tartrate | 10 | mg |
| Acetyl-L-carnitine | 5 | mg |
| Free Radical Scavenger Complex | | |
| Cruciferous vegetable concentrate (broccoli, kale, radish) (2% glucosinolates) | 40 | mg |
| Grape skin extract (37% total phenolics) | 20 | mg |
| Tomato lycopene extract (20% lycopene) | 2 | mg |
| Rosemary 4:1 extract (aerial parts) | 3.25 | mg |
| Pycnogenol (pine bark extract) | 1.65 | mg |
| Lutein (from marigold flower extract) | 0.8 | mg |
| Green barley grass | 10 | mg |
| DNA Repair Complex | | |
| Water extract of *uncaria tomentosa* (containing carboxy alkyl esters) | 125 | mg |
| Inositol hexaphosphate | 2 | mg |
| N-acetyl cysteine | 8 | mg |
| Melatonin | 0.5 | mg |
| Stem Cell Maintenance Complex | | |
| *Chlorella* algae | 25 | mg |
| *Spirulina* algae | 15 | mg |
| Klamath blue green algae | 45 | mg |
| Fucoxanthin seaweed (whole plant) | 25 | mg |
| Brown seaweed extract | 5 | mg |
| Cell Regulation Complex | | |
| Phosphatidylcholine (from soy lecithin) | 20 | mg |
| *Cordyceps sinensis* mushroom extract (1% cordycepic acid) | 8.25 | mg |
| Royal jelly 3x (5% 10-HDA) | 9 | mg |
| Inositol | 50 | mg |
| L-Glutamine | 250 | mg |
| L-Arginine (as L-arginine HCl) | 160 | mg |
| L-Ornithine (as L-ornithine HCl) | 120 | mg |
| Taurine | 16 | mg |
| L-Tyrosine | 20 | mg |
| Probiotic blend including *Lactobacillus acidophilus*, *Lactobacillus plantarum*, *Bifidobacterium bifidum* and *Lactobacillus casei* | 50 | million CFU |
| Amylase | 400 | units |
| Neutral protease | 100 | units |
| Lactase | 65 | units |
| Lipase | 16 | units |
| Vitamins | | |
| Vitamin A (as retinyl palmitate and 85% from natural mixed carotenoids) | 1,400 | IU |
| Vitamin C (as ascorbic acid and ascorbyl palmitate) | 200 | mg |
| Vitamin D (as cholecalciferol) | 30 | IU |
| Vitamin E (as d-alpha-tocopheryl succinate and from mixed natural tocopherols) | 40 | IU |
| Vitamin K (as phytonadione) | 75 | mcg |
| Thiamin (as thiamin HCl) | 2.5 | mg |
| Riboflavin (as riboflavin and riboflavin-5-phosphate) | 5 | mg |
| Niacin (as niacinamide and niacin) | 70 | mg |
| Vitamin $B_6$ (as pyridoxine HCl and pyridoxal-5-phosphate) | 7.5 | mg |
| Folate (as folic acid) | 80 | mcg |
| Vitamin $B_{12}$ (as cyanocobalamin) | 120 | mcg |
| Biotin | 40 | mcg |
| Pantothenic acid (as D-calcium pantothenate) | 20 | mg |
| Minerals | | |
| Iodine (as potassium iodide and from kelp) | 12 | mcg |
| Magnesium (as magnesium oxide and glycinate) | 132.5 | mg |
| Zinc (as zinc glycinate) | 1.5 | mg |
| Selenium (as selenomethionine) | 24 | mcg |

TABLE 4-continued

Example PM Dietary Supplement Composition

| Components | Amount Per Serving |
|---|---|
| Copper (as copper lysinate) | 0.1 mg |
| Manganese (as manganese gluconate) | 0.1 mg |
| Chromium (as chromium polynicotinate) | 40 mcg |
| Molybdenum (as sodium molybdate) | 8 mcg |

Other ingredients: Microcrystalline cellulose, croscarmellose sodium, stearic acid, calcium silicate, magnesium stearate, silica and film coat ingredients (hypromellose, hydroxypropyl cellulose, and polyethylene glycol).

All publications, patent applications, patents, and other references mentioned herein are incorporated by reference in their entirety.

While the invention has been disclosed in connection with certain preferred embodiments, this should not be taken as a limitation to all of the provided details.

Modifications and variations of the described embodiments may be made without departing from the spirit and scope of the invention, and other embodiments should be understood to be encompassed in the present disclosure as would be understood by those of ordinary skill in the art.

What is claimed is:

1. A dietary supplement system comprising:
   (i) a first dietary supplement composition for oral administration to an individual, said first composition comprising:
   (a) a telomere maintenance complex comprising:
   Purslane; Turmeric rhizome extract; Quercetin dehydrate; Cayenne pepper fruit; Vanadium (as vanadyl sulfate); Fenugreek seed; *Astragalus* root extract; and an Omega fatty acid complex, including linoleic acid, alpha-linolenic acid, oleic acid, borage seed oil, evening primrose oil, eicosapentaenoic acid and docosahexaenoic acid;
   (b) a calorie restriction mimetics and gene expression complex comprising:
   Trans-resveratrol; Pterostilbene (99%); Fisetin 50%; Alpha lipoic acid; Coenzyme Q-10; Betaine HCl; Sulfur; and L-Carnitine;
   (c) a free radical scavenger complex comprising:
   Green tea leaf extract; Anthocyanins; *Ginkgo biloba* leaf extract; and Green barley grass;
   (d) a DNA repair complex comprising:
   a Water extract of *Uncaria tomentosa*;
   (e) a stem cell maintenance complex comprising:
   *Chlorella* algae; *Spirulina* algae; Klamath blue-green algae; fucoxanthin-containing seaweed (whole plant); and Nori seaweed extractract;
   (f) a cell regulation complex comprising:
   Gotu kola leaf; Phosphatidyl choline; dimethylaminoethanol (DMAE); *Cordyceps sinensis* mushroom extract; Royal jelly 3× (5% 10-hydroxy-2-decenoic acid); L-Glutamine; Taurine; L-Phenylalanine; L-Tyrosine; Guarana seed extract; Amylase; Neutral protease; Cellulase; Lactase; and Lipase;
   (g) Vitamin K; and
   (h) a group of minerals comprising:
   Iodine; Calcium; Zinc; Selenium; Copper; Manganese; Chromium; and Molybdenum; and
   (ii) a second dietary supplement composition for oral administration to the individual, said second composition comprising:
   (a) a telomere maintenance complex comprising:
   Purslane extract; Turmeric rhizome extract; Quercetin dehydrate; Cayenne pepper fruit; Vanadium; Fenugreek seed; Valerian root extract; and an Omega fatty acid complex, including linoleic acid, alpha-linolenic acid, oleic acid, borage seed oil, evening primrose oil, eicosapentaenoic acid and docosahexaenoic acid;
   (b) a calorie restriction mimetics and gene expression complex comprising:
   Resveratrol; Pterostilbene; Fisetin 50%; Alpha-lipoic acid; Coenzyme Q10; Betaine; Sulfur; L-Carnitine tartrate; and Acetyl-L-Carnitine;
   (c) a free radical scavenger complex comprising:
   Cruciferous vegetable concentrate; Grape skin extract; Tomato lycopene extract; Rosemary extract; Pycnogenol; Lutein; and Green barley grass;
   (d) a DNA repair complex comprising:
   a Water extract of *Uncaria tomentosa*; Inositol hexaphosphate; N-acetyl cysteine; and Melatonin;
   (e) a stem cell maintenance complex comprising:
   *Chlorella* algae; *Spirulina* algae; Klamath blue green algae; Fucoxanthin-containing seaweed; and Brown seaweed;
   (f) a cell regulation complex comprising:
   Phosphatidyl choline; *Cordyceps sinensis* mushroom extract; Royal jelly 3×; Inositol; L-Glutamine; L-Arginine; L-Ornithine; Taurine; and L-Tyrosine;
   (g) Vitamin K; and
   (h) a group of minerals comprising:
   Iodine; Magnesium; Zinc; Selenium; Copper; Manganese; Chromium; and Molybdenum.

2. The supplement system of claim 1 further comprising a pharmaceutically acceptable medium.

3. The supplement system of claim 1 wherein the supplement is formulated for oral administration.

4. The supplement system of claim 3 wherein formulations for oral administration are powders, granules, capsules, tablets or liquids.

5. The supplement composition of claim 1 is for administration to subject in need of an anti-aging management system.

* * * * *